United States Patent [19]
Zinke et al.

[11] 4,197,209
[45] Apr. 8, 1980

[54] LUBRICANT COMPOSITIONS CONTAINING SULFUR-CONTAINING ESTERS OF PHOSPHORIC ACID

[75] Inventors: Horst Zinke, Ernsthofen; Joachim Lorenz, Bensheim, both of Fed. Rep. of Germany

[73] Assignee: Ciba-Geigy Corporation, Ardsley, N.Y.

[21] Appl. No.: 881,211

[22] Filed: Feb. 27, 1978

[30] Foreign Application Priority Data

Mar. 10, 1977 [CH] Switzerland ............... 3029/77

[51] Int. Cl.² .................. C07F 9/165; C10M 1/48
[52] U.S. Cl. .................. 252/46.6; 260/942; 260/976; 252/46.7
[58] Field of Search .................. 260/942; 252/46.6

[56] References Cited

U.S. PATENT DOCUMENTS

| | | | |
|---|---|---|---|
| 2,943,107 | 6/1960 | Rattenbury et al. | 260/976 |
| 3,374,291 | 3/1968 | Myers | 260/942 |
| 3,705,216 | 12/1972 | Farley | 260/970 |
| 3,773,716 | 11/1973 | Rattenbury | 260/45.85 |
| 3,922,325 | 11/1975 | Anderson | 260/972 |

FOREIGN PATENT DOCUMENTS 1137298  5/1957  France .................... 260/974

OTHER PUBLICATIONS

Mandel'baum et al., "Chem. Abs.", vol. 68, (1968), pp. 2821, 8350.
Houben-Weyl, vol. 12/2, pp. 93-95 and 742-748.
Schmiermittel Taschenbuch, Huthig Verlag, Heidelberg, (1974), vol. 15, pp. 229-232.

*Primary Examiner*—Anton H. Sutto
*Attorney, Agent, or Firm*—Luther A. R. Hall

[57] ABSTRACT

Trithio- and tetrathiophosphates with mercaptocarboxylic acid derivatives are preeminently suitable as extreme pressure additives for lubricants. They reduce signs of wear and have no or only an insignificant corrosive action on the parts to be protected.

16 Claims, No Drawings

LUBRICANT COMPOSITIONS CONTAINING SULFUR-CONTAINING ESTERS OF PHOSPHORIC ACID

The present invention relates to trithio- and tetrathiotriphosphates, processes for their production and the use thereof as additives for lubricants, as well as to a process for the production of trithiotriphosphites.

Sulphur-containing esters of phosphoric acid and phosphorous acid, processes for their production and the use thereof as lubricant additives have long been known in the art, cf. for example French Pat. No. 1,137,298 and Houben-Weyl, Methoden der organischen Chemie, Thieme Verlag, Vol. 12/2, pp. 93–95 and 742–748. In addition to other economically unimportant processes, the reaction of phosphorus trichloride, phosphoroxy chloride and thiophosphoryl chloride with mercaptans is described herein and it is also mentioned that this reaction does not proceed uniformly, results in the formation of by-products, and that the desired products are only obtained in insufficient yields. The use of an excess of mercaptan does result in a higher net yield, but the desired product then additionally contains by-products.

There has been no lack of attempts to improve the processes. For example in U.S. Pat. No. 3,705,216 it is suggested to react phosphine or alkylphosphines with organic disulphides to give the sulphur-containing esters mentioned at the outset. The drawbacks of this process are the use of toxic and to some extent expensive starting materials and the low yields, especially if the mercaptan additionally contains other reactive groups, for example ester groups.

The proposal is made in U.S. Pat. No. 3,922,325 to use catalytic amounts of water for the production of trialkyl thiophosphites from phosphorus trihalides and alkylmercaptans. The disadvantges of this proposal are that sufficiently economic reaction times are only attained at elevated temperatures and that water can cause the formation of undesired hydrolysis products.

U.S. Pat. No. 3,374,291 describes a process for the production of trithiophosphites in which the phosphorus trihalide and mercaptan used as starting materials are reacted in the presence of molar amounts of tertiary amines to bind the resulting hydrogen halide. After the reaction, the ammonium halide has to be removed from the reaction mixture—a procedure which can cause losses in yield and the formation of by-products through oxidation and hydrolysis.

Another method of obtaining the tri- and tetrathiophosphates is via the oxidation of trithiophosphites. In Houben-Weyl, op. cit., pp. 747 and 748, it is described that the reaction of these esters with sulphur results in the desired compounds. In U.S. Pat. No. 2,943,107, the proposal is made to oxidise the reaction mixture to obtain higher yields in the direct reaction of butylmercaptan with phosphorus trichloride after an 85 to 95% reaction. As the by-products are not removed before the oxidation, the resulting tributyl trithiophosphate contains by-products which contain phosphorus and sulphur. Air is preferably used as oxidant. The air oxidation must be carried out at elevated temperatures, in which process additional secondary reactions may occur. This oxidation process is therefore not particularly suitable for the production of purer compounds.

There is therefore a need for an improved process for the direct production of trithiophosphites which contain no or only insignificant amounts of other phosphorus-containing compounds. In addition, there is a need for an improved oxidation process for the production of trithiotriphosphates, which proceeds substantially without the formation of by-products at relatively low temperatures. It is an object of the present invention to provide these processes.

Among the known sulphur-containing esters of phosphoric acids, representatives have been developed which are effective EP/AW additives for lubricants. However, these esters are not without deficiencies. For example, triphenylthionophosphate often has only an insufficient activity. The trithiophosphites, especially the trithiophosphites from $PCl_3$ and SH-containing carboxylic acid esters described in U.S. Pat. No. 3,374,291, have a corrosive action on metal surfaces, particularly at elevated temperatures. The alkyl trithio- and tetrathiophosphates proposed in U.S. Pat. No. 3,705,216 are also deficient in their effectiveness. It is held to be a drawback of the effective zinc dialkyldithiophosphates that they do not burn without leaving any residue and therefore on account of the metal content and of the relatively low decomposition temperatures tend to form deposits, for example on contact with hot metal surfaces.

It is therefore a further object of the present invention to provide trithiotriphosphates and tetrathiotriphosphates which, by comparison, have improved or identical EP/AW action and do not have a corrosive action on metal surfaces and do not result in the formation of deposits or combustion residues on metal surfaces.

Accordingly, the invention provides trithiotriphosphates and tetrathiotriphosphates of the general formula I

$$XP(S-C_nH_{2n}-CO-R)_3 \qquad (I)$$

wherein

X represents an oxygen or sulphur atom, n is an integer from 1 to 6, and

R represents the group $R^1-O-$, wherein $R^1$ represents alkyl, cycloalkyl, aryl, cycloalkylalkyl or aralkyl which is unsubstituted or substituted by alkyl groups, or represents alkoxyalkyl or alkylthioalkyl, or R represents the group $R^2R^3N-$, wherein $R^2$ and $R^3$ have the same meanings as $R^1$, $R^2$ also represents a hydrogen atom and $R^2$ and $R^3$ together represent alkylene which can be interrupted by oxygen.

The $C_nH_{2n}$ group in formula I, in which n is preferably 2 and especially 1, can be linear or branched alkylene or alkylidene. Examples are in particular; methylene, ethylene and ethylidene, as well as 1,2- or 1,3-propylene, 1,1- or 2,2-propylidene, butylene, butylidene, pentylene, pentylidene, hexylene and hexylidene.

Preferred subgroups of the compounds of the formula I include those in which X represents an oxygen atom or R represents the group $R^1-O-$.

The alkyl group substituents in the radical $R^1-O-$ contain preferably 1 to 18, especially 1 to 12, carbon atoms. The substituents $R^1$, $R^2$ and $R^3$ contain preferably 1 to 24, especially 1 to 18 and most preferably 4 to 16, carbon atoms. Preferably $R^1$, $R^2$ and $R^3$ represent linear and especially branched alkyl.

$R^1$, $R^2$ and $R^3$ as cycloalkyl and cycloalkylalkyl contain 5 or 6 ring carbon atoms. Aryl is in particular phenyl and aralkyl is in particular benzyl.

In a preferred subgroup of the esters of the formula I, R represents the group $R^1$—O—, wherein $R^1$ represents linear and especially branched alkyl, cycloalkyl or cycloalkylalkyl which is unsubstituted or substituted by one or more alkyl groups, or is linear or branched alkoxyalkyl and alkylthioalkyl.

A further preferred subgroup of esters of the formula I comprises those of the formula II $$XP(SCH_2\text{—}CO\text{—}R)_3 \qquad (II)$$

wherein X represents a sulphur and especially an oxygen atom and R represents the group $R^1$—O—, in which $R^1$ is preferably branched alkyl containing in particular 3 to 16, most preferably 8 to 16, carbon atoms. Particularly preferred esters of this subgroup are those of the formulae $OP(SCH_2COO\text{-octyl})_3$ and $SP(SCH_2COO\text{-octyl})_3$.

$R^1$, $R^2$ and $R^3$ can represent alkyl which is linear or branched. Examples are: methyl, ethyl, n- or isopropyl, n-, iso- or tert-butyl, pentyl, hexyl, 2-ethylhexyl (isooctyl), heptyl, octyl, 2-propylpentyl, isononyl, isodecyl, decyl, 2-butylhexyl, 3-hexylpentyl, 3-methylundecyl, undecyl, isododecyl, dodecyl, 2-methyldodecyl, 2-ethyldecyl, 3-propyldecyl, 2-hexyldecyl, tetrahexyl, hexadecyl, iso-hexadecyl, 2-ethylhexyldecyl, iso-octadecyl, iso-eicosyl, eicosyl, octadecyl, 2-hexyltetradecyl, 2-ethyleicosyl, 2-butyloctadecyl.

In addition to straight chain alkyl radicals, branched alkyl radicals are also suitable which are derived from technical alcohols or mixtures of alcohols. The alcohols are usually manufactured industrially and are frequently mixtures of different unbranched or branched alcohols. These alcohols are commercially available, for example as alfols, dobanols and oxanols, and are a preferred group.

$R^1$, $R^2$ and $R^3$ can be cycloalkyl, cycloalkylalkyl, aryl and aralkyl which is unsubstituted or substituted by alkyl groups. Preferably the alkylene moiety of cycloalkylalkyl and aralkyl contains 1 to 3 carbon atoms, especially 1 carbon atom, and is preferably substituted by 1 to 2 alkyl groups. Examples are: phenyl, naphthyl, methylphenyl, dimethylphenyl, ethylphenyl, propylphenyl, butylphenyl, t-butylphenyl, methylbutylphenyl, hexylphenyl, dihexylphenyl, octylphenyl, i-octylphenyl, t-octylphenyl, nonylphenyl, nonylmethylphenyl, decylphenyl, dodecylphenyl, octadecylphenyl, dinoylphenyl, benzyl, methylbenzyl, dimethylbenzyl, ethylbenzyl, propyl- or i-propylbenzyl, n-, i- or t-butylbenzyl, octylbenzyl, nonylbenzyl, dodecylbenzyl, dioctylbenzyl, cyclohexyl, cyclohexylmethyl, methyl-, ethyl-, propyl-, butyl-, octyl-, nonyl-, decyl-, dodecyl-, dimethyl- or trimethylcyclohexyl or -cyclohexylmethyl.

$R^2$ and $R^3$, and especially $R^1$, can also be linear or branched alkoxyalkyl or alkylthioalkyl. The corresponding alcohols can be obtained in known manner by the addition of alcohols or mercaptans to epoxides, for example ethylene, propylene, butylene, pentylene, hexylene, cyclohexylene or styrene epoxides. A preferred group has the formula $$R^4\text{—}X\text{—}C_nH_{2n}\text{—}$$

wherein $R^4$ represents alkyl as defined for $R^1$, X represents an oxygen or sulphur atom and n is an integer from 2 to 6, especially 2.

The group $R^2R^3N$— for R in formula I can be a primary, especially secondary, amide group. $R^2$ and $R^3$ are preferably phenyl, cyclohexyl, cyclopentyl and linear or especially branched alkyl of preferably 1 to 12 carbon atoms. $R^2$ and $R^3$ together as alkylene contain 4 to 6 carbon atoms. Examples are: tetra-, penta- or hexamethylene and 3-oxapentylene.

The compounds of the invention can be prepared by the processes described hereinafter. They are mobile, viscous, wax-like to crystalline in consistency. They are surprisingly readily soluble in lubricants, especially those in which $R^1$, $R^2$ and $R^3$ in formula I represent a branched radical. They are preeminently suitable as enriching additives for lubricants, as they improve both the extreme pressure and the anti-wear properties surprisingly well. In addition to this excellent action, the compounds of the invention are virtually non-corrosive. The esters which are obtained by the process of the invention are virtually pure, i.e. they do not contain any amounts of other phosphorus-containing compounds which can be detected by $^{31}P$ nuclear resonance spectroscopy. Among the esters of the present invention, the trithiophosphates have surprisingly a still better action than the tetrathiophosphates.

The compounds of the formula I act even in very small amounts as extreme pressure additives in lubricants. Thus mineral and synthetic lubricant oils and mixtures thereof which contain 0.01 to 5% by weight, based on the lubricant, and preferably 0.1 to 3% by weight, of a compound of the formula I exhibit excellent extreme pressure lubricant properties which become evident from the markedly reduced signs of wear of the parts to be lubricated. The suitable lubricants are known to the skilled person and are described for example in the "Schmiermittel Taschenbuch" (Hüthig Verlag, Heidelberg, 1974). The lubricating oil can contain still further additives which are added to improve the performance properties, such as antioxidants, metal deactivators, rust inhibitors, viscosity index improvers, pour-point depressors, dispersants/detergents and other wear-resisting additives.

Examples of antioxidants are:

(a) Alkylated and non-alkylated aromatic amines and mixtures thereof, for example; dioctyldiphenylamine, mono-tert-octylphenyl-α- and -β-naphthylamines, phenotriazine, dioctylphenothiazine, phenyl-α-naphthylamine, N,N'-di-sec-butyl-p-phenylenediamine.

(b) Sterically hindered phenols, for example: 2,6-di-tert-butyl-p-cresol, 4,4'-bis-(2,6-diisopropylphenol), 2,4,6-triisopropylphenol, 2,2'-thio-bis-(4-methyl-6-tert-butylphenol), 4,4'-methylene-bis-(2,6-di-tert-butyl-phenol) or esters of 2-(3,5-di-tert-butyl-4-hydroxyphenyl)propionic acid with e.g. hexane-1,6-diol, thiodiethylene glycol, octadecanol and pentaerylthritol.

(c) Alkyl-, aryl- or aralkylarylphosphites, for example: trinonylphosphite, triphenylphosphite, diphenyldecylphosphite.

(d) Esters of thiodipropionic acid or thiodiacetic acid, for example: dilaurylthiodipropionate or dioctylthiodiacetate.

(e) Salts of carbamic and dithiophosphoric acids, for example: antimony diamyldithiocarbamate, zinc diamyldithiophosphate, zinc di-2-ethylhexyl-dithiophosphate, zinc di-2-methylpropyldithiophosphate.

(f) A combination of two or more of the above antioxidants, for example: an alkylated amine and a sterically hindered phenol.

Examples of metal deactivators are:

(a) for copper, for example benzotriazole, tetrahydrobenzotriazole, 2-mercaptobenzotriazole, 2,5-dimercaptothiadiazole, salicylidene propylenediamine, salts of salicylaminoguanidine;

(b) for lead, for example sebacid acid derivatives, quinizarine, propyl gallate;

(c) a combination of two or more of the above additives.

Examples of rust inhibitors are:

(a) Organic acids, the esters, metal salts and anhydrides thereof, for example: N-oleyl-sarcosine, sorbitan mono-oleate, lead naphthenate, dodecenylsuccinic anhydride.

(b) Nitrogenous compounds, for example:

I. Primary, secondary or tertiary aliphatic or cycloaliphatic amines and amine salts of organic and inorganic acids, for example oil-soluble alkylammonium carboxylates.

II. Heterocyclic compounds, for example substituted imidazolines and oxazolines.

(c) Phosphorus-containing compounds, for example: amine salts of phosphoric acid partial esters.

(d) Sulphur-containing compounds, for example: barium dinonylnaphthalenesulphonates, calcium petroleum sulphonates.

(e) Combinations of two or more of the above additives.

Examples of viscosity index improvers are:

polymethylacrylates, vinyl pyrrolidone/methacrylate copolymers, polybutenes, olefin copolymers.

Examples of pour-point depressors are:

polymethacrylates, alkylated naphthalene derivatives.

Examples of dispersants/detergents are:

polybutenylsuccinic imides, polybutenylphosphonic acid derivatives, superbasic magnesium, calcium and barium sulphonates and phenolates.

Examples of other wear resisting additives are:

compounds which contain sulphur and/or phosphorus and/or halogen, such as sulphurised vegetable oils, zinc dialkyldithiophosphates, tritolylphosphate, chlorinated paraffins, alkyl- and aryldisulphides. The esters of the invention, in general trithiotriphosphites, trithiotriphosphates or tetrathiotriphosphates, are obtained by a novel, improved process.

It is therefore a further object of the invention to provide a process for the production of trithiotriphosphites, trithiotriphosphates or tetrathiotriphosphates of the general formula III $$(X)_mP(SR')_3 \quad (III)$$

wherein m is 0 or 1, X represents an oxygen or sulphur atom and R' represents a hydrocarbon radical of aliphatic or aromatic character which can be interrupted by O, S,

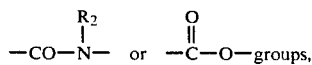

by (a) reaction of 1 mole of a phosphorus trihalide, preferably phosphorus trichloride, with 3 moles or a slightly less than equivalent amount or a slight excess of a mercaptan R'SH in the presence of a catalyst, and (b) subsequent oxidation of the resulting trithiotriphosphite with an oxygen donor or with sulphur for the production of the trithio- or tetrathiophosphates, which process comprises reacting the reactants in step (a) in the presence of a catalytic amount of a compound selected from the group consisting of the amines or ammonium salts, of the aromatic and non-aromatic nitrogen-containing heterocyclic compounds and the salts thereof, of the amides of carboxylic and thiocarboxylic acids and of the oxyacids of phosphorus, of the guanidines, amidines and azomethines as well as the salts thereof, of the sulphoxides, phosphines and phosphonium salts, of the phosphine oxides or esters of phosphoric acids.

The hydrocarbon radical R' in formula III contains preferably 1 to 24, especially 1 to 18 and most particularly 4 to 18, carbon atoms and is preferably linear or branched alkyl, alkoxyalkyl, alkylthioalkyl, alkyloxycarbonylalkyl, alkyloxycarbonylcycloalkyl or alkyloxycarbonylaryl, and optionally alkylated cycloalkyl or cycloalkylalkyl containing preferably 5 or 6 carbon atoms in the ring, and also aryl or aralkyl which preferably denote phenyl or benzyl respectively. Further preferred meanings follow from the definitions of $R^1$ and n in the esters of formula I. If the hydrocarbon radical R' is interrupted, it is interrupted preferably by oxygen, sulphur or the

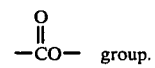

In the reaction step (a), a preferred molar ratio of $PX_3/R'SH$ is 1.03:3 to 1:3.3. Preferably, however, stoichiometric amounts are employed. Furthermore, this reaction can be carried out without solvents. It is however also possible to carry out the reaction in the presence of a solvent, for example a hydrocarbon, halogenated hydrocarbon or an ether, such as hexane, petroleum ether, benzene, xylene, toluene, methylene chloride, chloroform, carbon tetrachloride and diethyl ether, dioxane or tetrahydrofurane.

Effective amounts of the catalyst are at least 0.005, preferably at least 0.01, mol%, based on the mercaptan. It is advantageous to use not more than 5 mol%, preferably not more than 3 mol% and especially not more than 1 mol%.

The process of the invention is carried out in the presence of selected catalysts. The nitrogen atoms of the amines and ammonium salts, of the amides and nitrogen-containing heterocyclic compounds, of the guanidines, amidines and azomethines as well as the salts thereof, sulphoxides, phosphines, phosphonium salts, phosphine oxides and the esters of phosphoric acids, can contain alkyl, cycloalkyl, aryl, especially phenyl, aralkyl, especially benzyl, or aralkyl, especially alkylated benzyl, which preferably contain 1 to 18, especially 1 to 12, carbon atoms, and which may be interrupted by oxygen or sulphur atoms. Alkyl contains in particular 1 to 6 carbons and cycloalkyl is especially cyclopentyl and cyclohexyl.

The catalysts to be used as salts are preferably the halides and especially the chlorides. The salts can also be formed in situ as a result of the hydrogen halide formed in the process. It is likewise advantageous in some cases to use the salts themselves as catalysts.

The amines and ammonium salts form one group of catalysts. The amines can be primary, secondary and tertiary amines and the salts thereof. The salts also include the quaternary ammonium salts. The secondary amines, the salts thereof and the quaternary ammonium salts are preferred. Also preferred are the alkyl-substituted and cycloalkyl-substituted amines and the cyclic amines which are classified among the nonaromatic heterocyclic compounds.

Examples are: methyl-, ethyl-, propyl-, n-butyl-, tert-butyl-, pentyl-, octyl-, dodecyl-, phenyl-, benzyl-, dimethyl-, diethyl-, methylethyl-, methylbutyl-, methyloctyl-, methylphenyl-, ethylbenzyl-, trimethyl-, triethyl-, tributyl-, octyldimethyl- and dimethylphenylamine, as well as tetramethyl-, trimethylethyl-, triethylmethyl-, tributylmethyl-, tetrabutyl-, trimethyloctyl-, triphenylmethyl- and tribenzylmethylammonium chloride, bromide or iodide.

Examples of further ammonium salts are: methyl-, octyl-, dimethyl-, methylcyclohexyl-, dibenzyl-, diphenyl-, trimethyl-, tributyl-, tribenzyl-, and triphenylammonium chloride, bromide and iodide. The amines and ammonium salts can also contain aromatic N-heterocyclic radicals, for example pyridyl. These amines are more effective than the pure aromatic N-heterocyclic compounds.

The amides of carboxylic and thiocarboxylic acids and of phosphoroxy acids constitute a further group of catalysts. This group also includes the ureas, thioureas and their bisurea derivatives. The amides can be derived from polyfunctional, preferably monofunctional, carboxylic acids or thiocarboxylic acids which contain in particular 1 to 14 carbon atoms. The acids can also be derived from aromatic N-heterocyclic compounds. In addition, cyclic amides, for example $\epsilon$-caprolactam, are also suitable. The amides derived from carboxylic and thiocarboxylic acids preferably have the formula

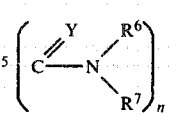

wherein, if n is 1, $R^5$ represents phenyl, benzyl, naphthyl, cyclohexyl, cyclopentyl, pyridyl, hydrogen or alkyl of 1 to 13, preferably 1 to 6, carbon atoms, and, if n is 2, $R^5$ represents phenylene, naphthylene, cyclohexylene or alkylene of 1 to 12, preferably 1 to 6, carbon atoms or is a direct bond, Y represents an oxygen or sulphur atom and each of $R^6$ and $R^7$ independently represents a hydrogen atom, phenyl, benzyl, cyclohexyl and alkyl of 1 to 12, preferably 1 to 6, carbon atoms, or $R^6$ and $R^7$ together represent alkylene of preferably 4 to 7 carbon atoms which may be interrupted by oxygen or sulphur atoms. Examples are: formamide, oxalic diamide, dimethyl formamide, acetamide, thioacetamide, N,N-dimethyl acetamide or thioacetamide, picoanilide, thiopicoanilide, benzoylamide, terephthalic diamide, trimellitic triamide.

The phosphorus oxyacids from which the amides can derive are for example phosphoric acid, phosphorous acid, hypophosphorous acid, phosphonic acid or phosphinic acid. Phosphoric acid and phosphonic acids are preferred. Examples of such amides are: phosphoric triamide, hexamethylphosphoric triamide, methylphosphonic diamide, phenylphosphonic N,N-tetramethyl diamide, N,N'-(dimethyl)phenylphosphonic diamide.

In addition to urea and thiourea, examples of amides of carbonic acid or thiocarbonic acid are: tetramethyl urea or thiourea, diphenyl or dibenzyl urea or thiourea, diethyl urea, di-n-octyl urea or thiourea, as well as bis-urea derivatives, for example ethylene bis-urea, N,N-tetramethylphenylene thiourea. Examples of cyclic ureas are hydantoin and benzimidazolone.

A further group of catalysts suitable for the process of the present invention are non-aromatic and aromatic N-heterocyclic compounds. These compounds can contain more than one nitrogen atom as well as oxygen and sulphur atoms. They can be in the form of salts, and also of quaternary ammonium bases and the nitrogen atoms and/or the ring carbon atoms can be substituted, preferably by alkyl groups of 1 to 12 carbon atoms. Examples of further substituents are: carboxyl, alkoxycarbonyl, amidocarbonyl. Examples of such compounds are: pyrrolidine, $\Delta^3$-pyrroline, N-methylpyrrolidine, dihydroindole, pyrazolidine, imidazolidine, $\Delta^2$-pyrazoline, 1-phenylpyrazolidine, oxazolidine, thiazolidine, oxazoline, triazolidine, oxadiazolidine, thiadiazolidine, piperidine, morpholine, N-methylmorpholine, quinolidine, 1,2-dihydropurine, 8-aza-bicyclo-(3,2,1)-octane, pyrrole, pyridine, indole, imidazole, pyrazole, oxazole, thiazole, triazole, benzotriazole, quinoline, pyridazine, pyrimidine, pyrazine, picoline, $\alpha$-aminopyridine, triazine, melamine.

Among the guanides, in addition to guanidine itself mention may be made of N-alkylated, benzylated and phenylated derivatives, for example tetramethyl- or tetrabutylguanidine, N,N'-bisphenylguanidine. Suitable salts are chiefly the halides.

A further group of catalysts comprises the azomethines and amidines and the salts thereof, preferably the halides. They can be illustrated by the following formulae:

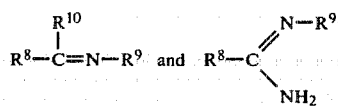

wherein each of $R^8$ and $R^9$ independently represents phenyl, benzyl, cyclohexyl, a hydrogen atom or alkyl of 1 to 8, preferably 1 to 4, carbon atoms and $R^{10}$ represents a hydrogen atom or phenyl, benzyl, cyclohexyl or alkyl of 1 to 18, preferably 1 to 8, carbon atoms. As examples there may be mentioned: acetamidine hydrochloride, N-methylacetamidine, benzylidene anilide, N-butylpropionamidine.

The sulphoxides used as catalysts can be linear or cyclic and they can contain further functional groups, for example ester groups. Examples are: dimethyl sulphoxide, tetramethylene sulphoxide, bis-carbo-isooctyloxy dimethyl sulphoxide.

A further group of catalysts to be used in the process of the present invention comprises the primary, secondary and tertiary phosphines, phosphonium salts and phosphine oxide. The tertiary phosphines, the salts thereof, the quaternary phosphonium salts and, among the salts, the hydrohalides, especially the chlorides, bromides and iodides, are preferred. The phosphorus atom can contain phenyl, benzyl, cyclohexyl and alkyl of 1 to 12, preferably 1 to 6, carbon atoms. Examples are: methylphosphine, ethylphosphine, hexylphosphine, dodecylphosphine, dimethyl-, ethylmethyl-, diphenyl-, dicyclohexyl-, dibenzyl-, phenylmethylphosphine, triphenyl-, tribenzyl-, tricyclohexyl-, trimethyl-, triethyl-, tripropyl-, tributyl-, triisobutyl-, tripentyl-, trihexyl-, dimethylphenylphosphine, the hydrochlorides, hydrobromides and hydroiodides and oxides thereof, tetramethyl-, tetrabutyl-, tetraphenyl-, triphenylmethyl- or trimethylphenylphosphonium chloride or bromide.

The esters of phosphoric acid are preferably derived from phosphonic acids and phosphoric acid. The alcohol radicals of the esters are preferably derived from phenols and especially $C_1$–$C_{18}$alkanols and also cycloalkanols, for example phenol, 2-methylphenol, cyclohexanol, methanol, ethanol, propanol, butanol, hexanol, octanol, iso-octanol, dodecanol, octadecanol. Examples of phosphonic acids are: phenyl-, benzyl-, cyclohexyl-, methyl-, ethyl-, propyl-, butyl-, pentyl- and hexylphosphonic acid.

The reaction is advantageously carried out in such a manner that the reactants and the catalyst are slowly mixed at low temperature, preferably below 35° C., especially between 0° and 30° C., and the reaction is brought to completion after a 10 to 60%, preferably 35 to 45%, reaction, determined from the amount of hydrogen halide evolved at a higher temperature, for example between 60° and 150° C., preferably between 80° and 120° C. The heating can also be effected in vacuo. The hydrogen halide which forms is advantageously removed continuously during the reaction. The trithiophosphites produced by the process of the invention are surprisingly obtained in virtually pure form direct without further purifying operations and in high yields. No other phosphorus-containing compounds as by-products are detected by the $^{31}$P-nuclear magnetic resonance method.

The trithiophosphites obtained according to the invention are used as such or are reacted without first being purified to give the tri- or tetrathiophosphates.

The latter are obtained in known manner by reacting the trithiophosphites with sulphur. Advantageously the same tertiary amines or corresponding hydrohalides are used as catalysts as were used in the production of the trithiophosphites. The known methods are described for example in Houben-Weyl, Methoden der organischen Chemie, Thieme-Verlag, Vol. 12/2, pages 747 and 748. The reaction is preferably carried out without a solvent and at temperatures from 80° to 150° C. To isolate the desired products, an organic solvent can be added to the cooled reaction mixture, which is then washed with aqueous bicarbonate solution, dried, and the solvent is then removed. A vacuum treatment can then follow at elevated temperatures, affording virtually pure tetrathiophosphates in high yields.

The trithiophosphites obtained according to the invention can also be oxidised direct to give the corresponding trithiophosphates. If air is used as oxidising agent at elevated temperatures, an incomplete reaction and the formation of by-products are often observed. It has surprisingly been found, and this is a further object of the invention, that the oxidation proceeds under mild conditions to form virtually pure trithiophosphates in high yield by using hydrogen peroxide for the oxidation and by keeping the reaction temperature between 0° and 80° C., preferably between 20° and 40° C. It is especially advantageous if the concentration of hydrogen peroxide in the reaction mixture is not more than 10% by weight, preferably from 1 to 3% by weight.

The oxidation can be effected without the addition of a solvent. However, it is advantageous to carry out the oxidation in the presence of an inert organic solvent, for example an aliphatic or aromatic hydrocarbon. Examples of such solvents are: pentane, hexane, cyclohexane, methylcyclohexane, heptane, petroleum ether, xylene, benzene and especially toluene.

The advantageous maximum concentration of hydrogen peroxide can be attained in different ways. Thus a concentrated, for example 30%, aqueous solution of $H_2O_2$ can be added to the trithiophosphite, which is optionally cooled and diluted with an inert solvent, so slowly that the temperature does not exceed 0° to 80° C., preferably 20° to 40° C.

However, it is particularly advantageous to add to the trithiophosphite, which is optionally diluted with an inert solvent, sufficient water that the amount of $H_2O_2$ necessary for the oxidation can be added in a more highly concentrated form so rapidly that the preferred maximum concentration is not exceeded. By this means it is also possible to carry out the process continuously.

The isolation of the desired trithiophosphate is effected in the conventional manner by separating the aqueous phase, washing the organic phase neutral, drying and optionally removing the solvent. A vacuum treatment at elevated temperature can additionally follow.

This reaction proceeds surprisingly in virtually quantitative yield under the mild conditions. It was not possible to detect either by-products or starting material by $^{31}$P-NMR spectroscopy.

The following Examples illustrate the invention in more detail.

EXAMPLE 1

Phosphorus trichloride is mixed at room temperature with the mercaptan in the molar ratio 1.03/3 or ⅓ and, optionally after addition of a catalyst, the mixture is stirred at the same temperature. The hydrogen chloride set free is absorbed in a receiver vessel with water and the acid content of the vessel is titrated with 0.1 N sodium hydroxide solution at intervals of 30 and 60 minutes respectively. To avoid substantial losses of phosphorus trichloride, the temperature of the reaction mixture is advantageously raised to 70°–150° C. only after a reaction of about 40%, determined from the amount of hydrogen chloride evolved. The reaction is brought to completion by a subsequent vacuum treatment at 70°–150° C. and the reaction product is freed from residual dissolved hydrogen chloride. It is evident from Table 1 that the addition of pyridine results in a substantial increase of the reaction rate at the same or reduced reaction temperature.

Table 1

| | Reaction: $PCl_3$ + 3 RSH (RS)$_3$ P + 3 HCl | | | | | |
|---|---|---|---|---|---|---|
| Mercaptan | $PCl_3$/RSH | Catalyst | Conc.[1] (mol. %) | Time (hrs.) | Temp. (°C.) | Reaction[1] (%) |
| $nC_{12}H_{25}SH$ (comparison) | 1.03/3 | — | — | 5.5 | 25 | 0.1 |
| | | | | 7.5 | 25 | 3.7 |
| | | | | 9.0 | 25 | 10.2 |
| | | | | 15.4 | 25 | 40.0 |
| $nC_{12}H_{25}SH$ (comparison) | 1.03/3 | $H_2O$ | 0.237[2] | 2.5 | 25 | 0.1 |
| | | | | 5.0 | 25 | 3.4 |
| | | | | 6.0 | 25 | 8.3 |

Table 1-continued

Reaction: $PCl_3 + 3\ RSH \rightarrow (RS)_3P + 3\ HCl$

| Mercaptan | $PCl_3$/RSH | Catalyst | Conc.[1] (mol. %) | Time (hrs.) | Temp. (°C.) | Reaction[1] (%) |
|---|---|---|---|---|---|---|
| $nC_{12}H_{25}SH$ | 1.03/3 | pyridine | 1.0 | 14.6 | 25 | 40.0 |
|  |  |  |  | 0.5 | 26 | 16.0 |
|  |  |  |  | 1.0 | 24 | 43.7 |
|  |  |  |  | 1.5 | 61 | 62.1 |
|  |  |  |  | 2.0 | 100 | 75.7 |
| $HS-CH_2CO_2iC_8H_{17}$ (comparison) | 1/3 | — | — | 1.5 | 66 | 0.9 |
|  |  |  |  | 2.5 | 71 | 4.3 |
|  |  |  |  | 3.5 | 74 | 15.2 |
|  |  |  |  | 4.5 | 76 | 28.3 |
|  |  |  |  | 5.5 | 77 | 40.8 |
| $HS-CH_2CO_2iC_8H_{17}$ | 1/3 | pyridine | 1.0 | 0.5 | 30 | 1.2 |
|  |  |  |  | 1.5 | 23 | 34.1 |
|  |  |  |  | 2.5 | 30 | 54.9 |
|  |  |  |  | 3.5 | 67 | 68.6 |
|  |  |  |  | 4.5 | 100 | 78.6 |

[1] Based on the mercaptan
[2] Corresponding tp 0.021% in accordance with U.S. Pat. No. specification 3,922,325.

EXAMPLE 2

0.01 to 2.5 mol% of catalyst, based on the mercaptan, is dissolved in 50 ml of a solution of n-dodecylmercaptan in xylene (3 mmols of RSH/ml). The solution is charged into a reaction vessel of the microhydrogenation apparatus of Marhan and treated with 10 ml of a phosphorus trichloride/xylene solution (5 mmol of $PCl_3$/ml).

After closing the feed openings, the reaction mixture is stirred with a magnetic stirrer at 28.5° C. and the time is measured in which 40 ml of hydrogen chloride gas evolves (normal pressure, 28.5° C.).

The measurements for different catalysts and concentrations are reported in Table 2; "to" denotes the reaction time without catalyst.

Table 2

| Experiment | Catalyst | Concentration (mol %) | $t_{cat}$ (min) | to/$t_{cat}$ |
|---|---|---|---|---|
|  |  |  | (to) |  |
| 1 | Comparison | — | 183.00 | — |
| 2 | benzylamine | 0.5 | 5.55 | 33.0 |
| 3 | benzylamine | 0.1 | 10.25 | 11.3 |
| 4 | dicyclohexylamine | 0.1 | 2.48 | 73.8 |
| 5 | diisopropylamine | 0.1 | 2.20 | 83.2 |
| 6 | N-methylaniline | 0.1 | 3.20 | 57.2 |
| 7 | N,N-dimethyl-2-ethyl-hexylamine | 0.1 | 7.50 | 24.4 |
| 8 | tribenzylamine | 0.5 | 7.45 | 24.6 |
| 9 | tribenzylamine | 0.1 | 13.05 | 14.0 |
| 10 | pyridine | 0.1 | 6.12 | 29.9 |
| 11 | α-picoline | 0.1 | 21.67 | 8.4 |
| 12 | p-dimethylamino-pyridine | 0.1 | 5.45 | 33.6 |
| 13 | tetrabutylammonium-chloride | 0.1 | 1.72 | 106.4 |
| 14 | tetrabutylammonium-chloride | 0.02 | 6.67 | 27.4 |
| 15 | N-methyl formamide | 0.1 | 15.77 | 11.6 |
| 16 | N,N-dimethyl formamide | 0.1 | 9.93 | 18.4 |
| 17 | benzylidenaniline | 2.5 | 1.58 | 115.8 |
| 18 | benzylidenaniline | 0.1 | 20.40 | 9.0 |
| 19 | tetramethylguanidine | 0.1 | 2.03 | 90.2 |
| 20 | thioacetamide | 0.1 | 3.52 | 52.0 |
| 21 | 1,5-diazabicyclo-(5,5,0)-undec-5-ene | 0.1 | 2.13 | 85.9 |
| 22 | benzotriazole | 0.5 | 103.35 | 1.8 |
| 23 | 2-aminothiazole | 0.5 | 38.72 | 4.7 |
| 24 | 2-methylimidazole | 0.1 | 38.25 | 4.8 |
| 25 | dimethyl sulphoxide | 2.5 | 57.34 | 3.2 |
| 26 | hexamethylphosphoric triamide (HMPT) | 0.1 | 24.62 | 7.4 |
| 27 | triphenylphosphine | 0.1 | 9.77 | 18.7 |
| 28 | tributylphosphine | 0.1 | 1.55 | 118.1 |
| 29 | tributylphosphine | 0.02 | 7.00 | 26.1 |
| 30 | tri-isobutylphosphine oxide | 0.1 | 5.73 | 31.9 |
| 31 | dimethyl methanephosphonate (DMMP) | 2.5 | 24.22 | 7.6 |
| 32 | dimethyl methanephosphonate (DMMP) | 0.1 | 108.82 | 1.7 |
| 33 | dibutylphosphite | 0.1 | 123.27 | 1.5 |
| 34 | tetraphenylphosphonium chloride | 0.5+ | 25.43 | 7.2 |
| 35 | tetraphenylphosphonium chloride | 0.1+ | 34.53 | 5.3 |
| 36 | tetrabutylphosphonium chloride | 0.1 | 1.18 | 155.1 |
| 37 | tetrabutylphosphonium chloride | 0.02 | 5.43 | 33.7 |
| 38 | tributyl-lauryl-phosphonium chloride | 0.02 | 3.37 | 54.3 |

+ Catalyst suspended

EXAMPLE 3

The reaction of phosphorus trichloride with n-laurylmercaptan in the molar ratio ⅓ is carried out in chloroform as solvent in accordance with Example 2 in the microhydrogenation apparatus of Marhan. The time is once again measured in which 40 ml of hydrogen chloride gas are evolved (normal pressure, 28.5° C.). The results are reported in Table 3.

Table 3

| Experiment | Catalyst | Concentration (mol %) | $t_{cat}$ (min) | to/$t_{cat}$ |
|---|---|---|---|---|
|  |  |  | (to) |  |
| 1 | Comparison | — | 32.84 | — |
| 2 | benzylamine | 0.1 | 4.53 | 7.3 |
| 3 | triphenylphosphine | 0.1 | 1.22 | 26.9 |
| 4 | N,N-dimethyl formamide | 0.1 | 4.17 | 7.9 |
| 5 | dimethyl methane-phosphonate | 2.5 | 10.65 | 3.1 |
| 6 | tributylphosphine | 0.01 | 3.87 | 8.5 |
| 7 | tetrabutylphosphonium chloride | 0.01 | 3.22 | 10.2 |
| 8 | tetraphenylphosphonium chloride | 0.01 | 3.03 | 10.8 |

EXAMPLE 4

Phosphorus trichloride is reacted with n-dodecylmercaptan in accordance with Example 1. The results of the reaction measurements for different catalysts in comparison with a non-catalysed reaction are reported in Table 4.

Table 4

| Experiment | Molar ratio of $PCl_3/C_{12}H_{25}SH$ | Catalyst | Concentration* of catalyst (mol %) | time (hrs.) | temp. (°C.) | reaction (% of theory) |
|---|---|---|---|---|---|---|
| 1 | 1.03/3 | pyridine | 3 | 0.5 | 26 | 16.0 |
|   |        |          |   | 1.0 | 24 | 43.7 |
|   |        |          |   | 2.0 | 100 | 75.7 |
| 2 | 1.03/3 | N,N-dimethyl formamide | 3 | 0.5 | 26 | 34.1 |
|   |        |          |   | 1.0 | 23 | 55.6 |
|   |        |          |   | 2.0 | 100 | 77.2 |
| 3 | 1/3.15 | N-methylmorpholine | 2 | 0.5 | 26 | 8.2 |
|   |        |          |   | 1.5 | 22 | 47.1 |
|   |        |          |   | 2.5 | 107 | 78.4 |
| 4 | 1.03/3 | triethylamine | 5 | 0.5 | 26 | 37.7 |
|   |        |          |   | 1.0 | 23 | 59.1 |
|   |        |          |   | 2.0 | 100 | 77.4 |
| 5 | 1.03/3 | — | — | 5.5 | 25 | 0.1 |
|   |        |   |   | 7.5 | 25 | 3.7 |
|   |        |   |   | 15.4 | 25 | 40.0 |

*based on $PCl_3$

EXAMPLE 5

Tri-n-dodecyl trithiophosphite

To a mixture of 1314.4 g (6 moles) of n-dodecylmercaptan and 4.4 g (60 mmols) of diethylamine are added 283 g (2.06 moles) of phosphorus trichloride at room temperature in the course of 30 minutes and the mixture is stirred for 30 minutes at the same temperature. With stirring, the temperature is then raised in the course of 2½ hours to 150° C., a water jet vacuum is applied and stirring is continued for 3½ hours at 150° C. During this time a weak flow of nitrogen is introduced through a capillary.

The cooled reaction mixture is washed with two 160 ml portions of a solution of 8 g of sodium sulphate in 5% sodium hydroxide solution and then with two 160 ml portions of 5% sodium sulphate solution at room temperature, dried by vacuum treatment at 50°–100° C. and filtered after the addition of activated carbon and filter aid.

Yield: 1214 g (96%) of a colourless liquid which solidifies to a crystalline substance after prolonged standing at room temperature.

$n_D^{25}$: 1.5009
$D^{25}$: 0.910
acid number: 0.1 mgKOH/g
$^{31}$P-NMR signal −117.3 ppm.

EXAMPLE 6

Triphenyl trithiophosphite

With stirring, a mixture of 166.9 g (1.5 moles) of thiophenol and 0.99 g (7.5 mmols) of tetramethyl thiourea is treated at 1°–5° C. in the course of 30 minutes with 68.7 g (0.5 mole) of phosphorus trichloride, whereupon a vigorous evolution of hydrogen chloride gas takes place spontaneously. The temperature is raised in the course of 1½ hours to 150° C., a water jet vacuum is applied and stirring is continued for 1 hour at 150° C. The cooled reaction mixture is taken up in 120 ml of toluene, treated with activated carbon and, after addition of a filter aid, filtered hot.

The solvent is subsequently distilled off in vacuo almost completely and 120 ml of isopropanol are added to the residue. The trithiophosphite which has precipitated on cooling is collected by filtration, washed with toluene and isopropanol and dried in vacuo at 50° C.

Yield: 155.2 g (87% of theory) of colourless crystals.
Melting point: 73°–77° C.
Acid number: 0.6 mg of KOH/h
$^{31}$P-NMR signal: −133.0 ppm.

EXAMPLE 7

Tris-carbo-isooctyloxy-methyl trithiophosphite

With vigorous stirring, 206 g (1.5 moles) of phosphorus trichloride are added dropwise at room temperature in the course of 2 hours to a mixture of 918.8 g (4.5 moles) of isooctyl thioglycolate and 3.56 g (0.045 mole) of pyridine. The reaction mixture is then heated to 100° C. in the course of 2 hours and stirred for 2 hours at this temperature. After the evolution of hydrogen chloride has ceased a vacuum is applied, whereupon the pressure in the reaction vessel gradually falls to 16 mmHg. The pressure is then reduced to 0.1 mmHg and the mixture is stirred for 1½ hours at 100° C. A colourless liquid is obtained in quantitative yield.

$n_D^{20}$: 1,5031
$^{31}$P-NMR signal: −122.4 ppm

| Elemental analysis: | % P | % S |
|---|---|---|
| calculated | 4.8 | 15.0 |
| found | 4.7 | 15.0 |

EXAMPLE 8

Tris-carbo-(trimethylcyclohexyl)-oxymethyl trithiophosphite 324.6 g (1.5 moles) of trimethylcyclohexyl thioglycolate are reacted with 68.7 g (0.5 mole) of phosphorus trichloride in the presence of 1.23 g (14 mmols) of piperidine in accordance with the particulars of Example 7, affording a viscous, light yellow liquid in quantitative yield.

$n_D^{20}$: 1.5239
$^{31}$P-NMR signal: −121.9 ppm

| Elemental analysis: | % C | % H | % P | % S |
|---|---|---|---|---|
| calculated | 58.4 | 8.5 | 4.6 | 14.2 |

-continued

| Elemental analysis: | % C | % H | % P | % S |
|---|---|---|---|---|
| found | 58.6 | 8.6 | 4.3 | 14.5 |

EXAMPLE 9

S,S,S-tris-carbo-isooctyloxy-methyl trithiophosphate (1)

The reaction mixture of Example 7, which is cooled to room temperature, is diluted with 750 ml of toluene and, with vigorous stirring, oxidised with 186 g (1.64 moles) of 30% hydrogen peroxide solution (temp. ≦35° C.) after addition of 750 ml of water. After separation of the aqueous phase, the reaction mixture is washed with two 400 ml portions of sodium hydrogen carbonate solution and then with 400 ml of water and dried over sodium sulphate. The solvent is evaporated and the residue is then stirred for 1 hour at 100° C./0.1 mmHg.

Yield: 881 g (89% of theory)
Colourless liquid $n_D^{20}$: 1.4985
$^{31}$P-NMR signal at −62,1 ppm

| Elemental analysis: | % P | % S |
|---|---|---|
| calculated | 4.7 | 14.6 |
| found | 4.5 | 14.8. |

EXAMPLE 10

S,S,S-tris-carbo-isooctyloxy-methyl tetrathiophosphate (2)

48.1 g (1.5 moles) of sulphur are added to the reaction product of Example 7 and the mixture is heated in the course of 1 hour to 100° C., and stirred for 6 hours at 100° C. and for a further 2 hours at 120° C. After cooling to room temperature, the reaction mixture is diluted with 750 ml of toluene and washed with two 400 ml portions of sodium hydrogen carbonate solution and then with 400 ml of water and dried over sodium sulphate.

The solvent is removed and the residue is subjected to a vacuum treatment at 100° C./0.1 mmHg (2 hours) and at 120° C./0.1 mmHg (1½ hours), then filtered after addition of activated carbon and filter aid.

Yield: 887 g (88% of theory)
Light yellow liquid $n_D^{20}$: 1,5159
$^{31}$P-NMR: signal at −91.7 ppm

| Elemental analysis: | % P | % S |
|---|---|---|
| calculated | 4.6 | 19.1 |
| found | 4.6 | 18.9. |

EXAMPLES 11–20

The novel compounds listed in Table 2 are synthesised in accordance with the particulars of Examples 7 to 10.

Table 2

| Example | Compound | $n_D^{20}$ | m.p. | Elemental-analysis (calc./found) % P | % S |
|---|---|---|---|---|---|
| 11 | $(CH_3-O-\underset{\underset{O}{\|}}{\overset{\|}{C}}-CH_2-S)_3P=O$ | 1.5539 | — | 8.5 / 8.0 | 26.5 / 26.7 |
| 12 | $(nC_3H_7-O-\underset{\underset{O}{\|}}{\overset{\|}{C}}-CH_2-S)_3P=O$ | 1.5205 | — | 6.9 / 6.4 | 21.5 / 21.8 |
| 13 | $(C_2H_5-O-\underset{\underset{O}{\|}}{\overset{\|}{C}}-\underset{CH_3}{\overset{\|}{CH}}-S)_3P=O$ | 1.5141 | — | 6.9 / 6.6 | 21.5 / 21.8 |
| 14 | $(C_2H_5-O-\underset{\underset{O}{\|}}{\overset{\|}{C}}-CH_2CH_2-S)_3P=O$ | 1.5246 | — | 6.9 / 7.0 | 21.5 / 21.5 |
| 15 | $(C_6H_5-\underset{CH_3}{\overset{\|}{N}}-\underset{\underset{O}{\|}}{\overset{\|}{C}}-CH_2-S)_3P=O$ | — | 90°–91° C. | 5.3 / 5.4 | 16.4 / 17.0 |
| 16 | $(C_4H_9-O-C_2H_4-O-\underset{\underset{O}{\|}}{\overset{\|}{C}}-CH_2S)_3P=O$ | 1.5025 | — | 5.0 / 4.8 | 15.5 / 15.6 |
| 17 | $(2,6-(CH_3)_2-4-CH_3-C_6H_2-O-\underset{\underset{O}{\|}}{\overset{\|}{C}}-CH_2-S)_3P=O$ | highly viscous oil | — | 4.5 / 4.1 | 13.9 / 13.7 |
| 18 | $(iC_{16}H_{33}-O-\underset{\underset{O}{\|}}{\overset{\|}{C}}-CH_2-S)_3P=O$ | 1.4857 | — | 3.1 / 2.4 | 9.7 / 9.9 |
| 19 | $(CH_3-O-\underset{\underset{O}{\|}}{\overset{\|}{C}}-CH_2-S)_3P=S$ | 1.5888 | — | 8.2 / 7.8 | 33.9 / 34.2 |
| 20 | $(C_6H_5-\underset{CH_3}{\overset{\|}{N}}-\underset{\underset{O}{\|}}{\overset{\|}{C}}-CH_2-S)_3P=S$ | — | 88°–89° C. | 5.1 / 5.1 | 21.2 / 19.6 |

EXAMPLE 21

To test the extreme pressure/antiwear action, the compounds 1 and 2 are incorporated in a non-doped mineral lubricating oil (viscosity 116.26 cS/37.8° C.) and tested in a Shell fourball apparatus in accordance with DIN 51 350 ($\triangleq$ IP 239/69). For comparison, the non-doped mineral oil without additive and mixtures of this lubricant with commercially available EP/AW additives are also tested. The test results are reported in Table 3.

Table 3

| Additive | Concentration (% by weight) | ISL[1] (kg) | WL[2] (kg) | WSD[3] (mm) |
|---|---|---|---|---|
| — | — | 60 | 160 | 2.32 |
| 1 | 1.0 | 100 | 220 | 0.79 |
| 2 | 1.0 | 120 | 235 | 0.83 |
| triphenylthionophosphate | 1.0 | 105 | 165 | 2.17 |
| ZDTP[4] | 1.0 | 105 | 210 | 0.76 |

[1] initial seizure load
[2] weld load
[3] wear scar diameter (test conditions: 70 kg/1 hour)
[4] commercial zinc dialkyldithiophosphate As the test results show, the trithio- and tetrathiophosphates of the invention have a comparable or distinctly better action compared with commercially available EP/AW additives.

EXAMPLE 22

The excellent load bearing capacity of the trithio- and tetrathiophosphates of the invention is also evident in the test on the gearwheel deformation test stand of the "Forschungsstelle fur Zahnräder und Getriebe" (FZG). As additive, the phosphate 2 and, for comparison, commercially available EP/AW additives, are incorporated in a non-doped mineral lubricating oil (viscosity 33.45 cS/37.8° C.) and tested on the gearwheel deformation test stand in accordance with DIN 51 354 until the occurrence of failure under load. The values determined are the total abrasion of the gearwheels ($\Sigma\Delta m$), the specific abrasion ($\Delta m_s$) and the failure under load (FL) after the sudden change to heavy wear and tear. The results of this test are reported in Table 4.

Table 4

| Additive | Concentration (% by weight) | $\Sigma\Delta m$ (mg) | $\Delta ms$ (mg/PSh) | FL | Comments |
|---|---|---|---|---|---|
| — | — | 84.6 | 2.0 | 7 | no corrosion |
| 2 | 1.0 | 12.0 | < 0.1 | > 12 | no corrosion |
|  | 0.5 | 77.3 | 0.2 | 10 |  |
| triphenylthionophosphate | 1.0 | 332.0 | 0.19 | 9 | no corrosion |
| ZDTP[1] | 1.0 | 23.0 | 0.12 | > 12 | no corrosion |
|  | 0.5 | 88.0 | 0.21 | 11 |  |
| S,S,S-triscarboiso-octyl-oxymethyl trithiophosphite[2] | 1.0 | +15.8 | — | > 12 | strong film formation and corrosion |

[1] commercial zinc dialkyldithiophosphate
[2] cf. U.S. Pat. No. 3,374,291

The excellent extreme pressure properties of the phosphoric acid esters of the present invention, even when used in low concentration, are observed in the reduced total friction, a low specific wear and an improved load bearing capacity.

Compared with the phosphoric acid esters of the invention, corresponding trithiophosphites have the drawback of causing strong corrosion and film formation on the entire surface of the test gear wheels: this is also evident, inter alia, from the observed increase in weight of the gearwheels.

EXAMPLE 23

For comparison purposes, the phosphoric acid esters (1) and (2) and S,S,S-trilauryl trithiophosphate (I) as well as S,S,S-tri-n-butyl tetrathiophosphate (II) are incorporated in a non-doped mineral lubricating oil (viscosity 33.45 cS/37.8° C.) and tested on the gearwheel deformation test stand of the FZG (see Example 22) in accordance with DIN 51 354 until the occurrence of failure under load.

Table 5

| Additive | Concentration % | $\Sigma\Delta m$ (mg) | $\Delta ms$ mg/PS.h | FL | m-Val/100 g % oil P | S |
|---|---|---|---|---|---|---|
| — | — | 84,6 | 2,0 | 7 | — | — |
| 1 | 0.50 | 7.7 | < 0.1 | > 12 | 0.76 | 2.28 |
| 1 | 0.25 | 137.5 | < 0.1 | 12 | 0.38 | 1.14 |
| 2 | 0.50 | 77.3 | 0.2 | 10 | 0.74 | 2.97 |
| I[1] | 0.25 | 283.5 | 0.72 | 7–8 | 0.38 | 1.15 |
| II[1,2] | 0.50 | 414.9 | 0.17 | 9–10 | 1.51 | 6.05 |
| II | 0.245 | 210.1 | 0.54 | 8 | 0.74 | 2.96 |

[1] cf. U.S. Pat. No. 3,705,216
[2] cf. FR patent 1,137,298

The clear superiority of the trithio- and tetrathiophosphates of the invention compared with triaklkyl trithio- and tetrathiophosphates of the prior art is observed in the reduced total friction, a reduced specific wear and an improved load bearing capacity—increase in the level at which failure under load occurs—when applied in the same weight and P/S concentration.

The distinctly improved effectiveness of the trithiophosphates of the invention compared with the tetrathiophosphates of the invention can also be observed.

What is claimed is:

1. A lubricant composition comprising a mineral oil, a synthetic lubricant or mixture thereof and 0.01 to 5% by weight, based on the lubricant, of a compound of formula I

 (I)

wherein
X represents an oxygen or sulphur atom,
n is an integer from 1 to 6, and R represents the group R¹—O—, wherein R¹ represents alkyl; alkoxyalkyl or trimethylcyclohexyl.

2. A composition according to claim 1 wherein n is 1 or 2.

3. A composition according to claim 2 wherein n is 1.

4. A composition according to claim 1 wherein X is an oxygen atom.

5. A composition according to claim 1 wherein R¹ is alkyl of 1 to 18 carbon atoms.

6. A composition according to claim 5 wherein R¹ is alkyl of 1 to 12 carbon atoms.

7. A composition according to claim 1 wherein R¹ is linear or branched alkyl of 3 to 16 carbon atoms.

8. A composition according to claim 1 wherein the compound of formula I is selected from the group consisting of OP(SCH$_2$COO—Octyl)$_3$, SP(SCH$_2$COO—Octyl)$_3$, OP(SCH$_2$—COOC$_2$H$_4$—O—C$_4$H$_9$)$_3$ and OP(SCH$_2$COO—3,3,5-trimethylcyclohexyl)$_3$.

9. A method of improving the lubricant performance of a lubricant composition which comprises
incorporating into said lubricant composition comprising a mineral oil, synthetic lubricant or mixture thereof from 0.01 to 5% by weight, based on the lubricant, of a compound of formula I $$XP(S-C_nH_{2n}-CO-R)_3 \qquad (I)$$

wherein
X represents an oxygen or sulphur atom,
n is an integer from 1 to 6, and
R represents the group R¹—O—, wherein R¹ represents alkyl; alkoxyalkyl or trimethylcyclohexyl, 10. A method accoridng to claim 9 wherein n is 1 or 2.

11. A method according to claim 10 wherein n is 1.

12. A method according to claim 9 wherein X is an oxygen atom.

13. A method according to claim 9 wherein R¹ is alkyl of 1 to 18 carbon atoms.

14. A method according to claim 9 wherein R¹ is alkyl of 1 to 12 carbon atoms.

15. A method according to claim 9 wherein R¹ is linear or branched alkyl of 3 to 16 carbon atoms.

16. A method according to claim 9 wherein the compound of formula I is selected from the group consisting of
OP(SCH$_2$COO—Octyl)$_3$, SP(SCH$_2$COO—Octyl)$_3$, OP(SCH$_2$—COOO$_2$H$_4$—O—C$_4$H$_9$)$_3$ and OP(SCH$_2$COO-3,3,5-trimethylcyclohexyl)$_3$.

* * * * *